United States Patent [19]

Patnaik et al.

[11] Patent Number: 5,021,598

[45] Date of Patent: Jun. 4, 1991

[54] PROCESS FOR MAKING BISMUTH CARBOXYLATES

[75] Inventors: Prabodh K. Patnaik, Warren; Paul L. Cells, Cleveland, both of Ohio

[73] Assignee: Mooney Chemicals, Inc., Cleveland, Ohio

[21] Appl. No.: 384,245

[22] Filed: Jul. 24, 1989

[51] Int. Cl.$^5$ .................................................. C07F 9/94
[52] U.S. Cl. ........................................ 556/77; 556/64; 556/78; 502/170
[58] Field of Search .................. 556/64, 77, 78, 79; 502/170

[56] References Cited

U.S. PATENT DOCUMENTS

| | | | |
|---|---|---|---|
| 305,524 | 9/1884 | Mathieu | 556/77 |
| 1,580,592 | 4/1926 | Eichholz et al. | 556/78 |
| 1,933,520 | 10/1933 | Bruson | 134/57 |
| 1,991,783 | 2/1935 | Bockmuhl et al. | 260/11 |
| 2,044,968 | 6/1936 | Bruson | 260/11 |
| 2,058,403 | 3/1937 | Bockmuhl et al. | 260/11 |
| 2,087,999 | 6/1937 | Salzberg | 260/11 |
| 2,090,201 | 8/1937 | Herrmann et al. | 260/11 |
| 2,110,473 | 3/1938 | Salzberg | 260/11 |
| 2,150,349 | 3/1939 | Johannes et al. | 260/438 |
| 2,152,744 | 4/1939 | Kalman | 260/105 |
| 2,198,357 | 4/1940 | Vargha | 260/447 |
| 2,220,638 | 11/1940 | Boedecker et al. | 260/447 |
| 2,251,798 | 8/1941 | Meidert et al. | 106/310 |
| 2,252,665 | 8/1941 | Reiff et al. | 260/429 |
| 2,284,126 | 6/1942 | Bruson | 260/447 |
| 2,346,155 | 4/1944 | Denison et al. | 252/32 |
| 2,376,313 | 5/1945 | Reiff | 260/429 |
| 2,395,307 | 2/1946 | Weber et al. | 260/414 |
| 2,409,678 | 10/1946 | Hamblet | 260/414 |
| 2,416,074 | 2/1947 | Weber et al. | 260/414 |
| 2,480,823 | 9/1949 | Morris et al. | 252/42.7 |
| 2,843,555 | 7/1955 | Berridge | 260/18 |
| 3,133,942 | 5/1964 | Hahl | 260/414 |
| 3,211,768 | 10/1965 | Considine | 260/414 |
| 3,245,959 | 4/1966 | Roeser | 260/75 |
| 3,247,050 | 4/1966 | Leebrick | 556/69 |
| 3,365,403 | 1/1968 | Szczepanek et al. | 252/400 |
| 3,673,229 | 6/1972 | Rinse | 260/429 R |
| 3,678,087 | 7/1972 | Schmerling | 260/435 R |
| 3,962,298 | 6/1976 | Cukor et al. | 260/447 |
| 4,029,682 | 6/1977 | Foulks, Jr. | 260/414 |
| 4,083,807 | 4/1978 | McKinney et al. | 252/455 |
| 4,093,649 | 6/1978 | Kao et al. | 260/530 N |
| 4,162,986 | 7/1979 | Alkaitis et al. | 262/33.2 |
| 4,278,610 | 7/1981 | Maurer et al. | 260/438.1 |
| 4,337,208 | 6/1982 | Petronella | 260/414 |
| 4,404,408 | 9/1983 | Wirth et al. | 556/64 X |
| 4,438,038 | 3/1984 | Petronella | 260/414 |
| 4,469,636 | 9/1984 | Goel | 556/77 X |
| 4,584,362 | 4/1986 | Leckart et al. | 528/55 |
| 4,633,001 | 12/1986 | Cells | 556/44 |
| 4,649,065 | 3/1987 | Hein et al. | 427/370 |
| 4,742,090 | 5/1988 | Hunter et al. | 521/124 |
| 4,786,655 | 11/1988 | Grogler et al. | 521/93 |
| 4,808,407 | 2/1989 | Hein et al. | 424/141 |

FOREIGN PATENT DOCUMENTS 2019865 11/1979 United Kingdom .

*Primary Examiner*—Arthur G. Prescott
*Attorney, Agent, or Firm*—Renner, Otto, Boisselle & Sklar

[57] ABSTRACT

An improved process for making a bismuth carboxylate is disclosed which generally comprises (A) heating an anhydrous reaction mixture comprising a carboxylic acid or anhydride, bismuth metal, and hydrazine to a temperature of from about 80° C. up to, but not including, the temperature of decomposition of any reactant, hydrazine, or the desired bismuth carboxylate, (B) bubbling an oxygen-containing gas through the reaction mixture during (A), and (C) removing water formed during (B) from the reaction mixture. Bismuth carboxylate compositions are also disclosed which contain at least 70 equivalents of a bismuth carboxylate derived from at least one carboxylic acid or anhydride having from about 6 to about 20 carbon atoms, the composition having a viscosity of not more than 1000 centipoise at 25° C.

35 Claims, No Drawings

PROCESS FOR MAKING BISMUTH CARBOXYLATES

TECHNICAL FIELD

The present invention relates to an improved method for preparation of bismuth carboxylates.

BACKGROUND OF THE INVENTION

Many types and mixtures of metal salts and soaps of natural or synthetic organic acids, particularly carboxylic acids, have been suggested and commercially offered over several decades. These have been used to supply metals in forms which are soluble in organic liquids, especially in various hydrocarbon oils and solvents, to form solutions having various desired properties and uses. For example, such metal salts have found use as catalysts, or as fuel and lubricant additives.

Bismuth carboxylates have achieved notoriety as a catalyst system for preparing polyurethane elastomers. U.S. Pat. Nos. 4,584,362 and 4,742,090 provide detailed examples of how to use bismuth salts of carboxylic acids having from 2 to about 20 or 30 carbon atoms, respectively, and these patents are incorporated herein by reference.

It is also known that the preparation of polyurethanes from diisocyanates containing uretdione rings may be catalyzed by the presence of a bismuth salt of an organic carboxylic acid preferably having from 2 to 20 carbon atoms, such as disclosed in U.S. Pat. No. 4,786,655 incorporated herein by reference.

Other catalytic applications for bismuth soaps include curing organosiloxanes (U.S. Pat. No. 2,843,555), copolyesterification of terephthalic acid (U.S. Pat. No. 3,245,959) and oxidation of unsaturated aldehydes (U.S. Pat. No. 4,093,649).

Another field of use for this class of compounds is in the area of treatment of cracking catalysts. U.S. Pat. No. 4,083,807 discloses an improved catalytic cracking catalyst obtained by incorporating into a crystalline aluminosilicate catalyst by ion exchange a substantial concentration of a metal selected from the group consisting of antimony, bismuth and manganese, wherein the ion exchange is conducted with organic salts of antimony, bismuth and manganese.

Metal salts from polyvalent metals, such as mercury, copper, and bismuth may be used as driers in a drying oil composition which, when applied in the form of paints or coatings, can repel marine organisms and prevent mold and decay as disclosed in U.S. Pat. No. 1,933,520.

As various organic carboxylic acids have become available in commercial quantities, either from new natural sources, or as synthetic acids or standardized synthetic acid mixtures, the possibility of using these to produce metallic salts or soaps has been motivated, for example, by a lower price, by a relative uniformity of the commercial acids, by a better color or noncolor, by higher solubility of the salt products in various solvents in other components of ultimate products for which the metal salt is to be used, or stability in storage of the metal compositions or of their solutions. Bismuth carboxylates are an attractive non-toxic alternative to toxic metal catalysts and paint driers (such as cadmium and lead containing catalysts and driers). Neutral salt or soap compositions contain one mole of a carboxylate group per equivalent of metal present.

An early disclosure of a method for producing metal salts of organic acids using saturated aliphatic monocarboxylic acid having 1 to 8 carbon atoms, a metal having a normal potential between −0.80 and +0.5 volt, and an oxygen-containing gas as an oxidizing agent may be found in U.S. Pat. No. 3,133,942.

SUMMARY OF THE INVENTION

The present invention relates to a process for producing bismuth salts of at least one organic carboxylic acid. The process involves:

(A) heating an anhydrous reaction mixture comprising a carboxylic acid or anhydride, bismuth metal, and a reducing agent to a temperature of from about 80° C. up to, but not including, the temperature of decomposition of any reactant, the reducing agent or the desired bismuth carboxylate;

(B) bubbling an oxygen-containing gas through the reaction mixture during (A); and (C) removing water formed during (B) from the reaction mixture and/or reaction product.

Another aspect of the present invention is a liquid composition having a viscosity of not more than 1000 centipoise comprising at least one bismuth carboxylate derived from at least one carboxylic acid or anhydride having from about 6 to about 20 carbon atoms wherein the at least one bismuth carboxylate is present in an amount of at least about 70 weight-percent in terms of the neutral bismuth carboxylate.

DESCRIPTION OF THE PREFERRED EMBODIMENTS

The disclosed method comprises providing an anhydrous reaction mixture comprising a carboxylic acid or anhydride, bismuth metal, and a reducing agent. The mixture is heated to a temperature of from about 80° C. up to, but not including, the temperature of decomposition of any reactant, hydrazine, or the desired bismuth carboxylate and the mixture is bubbled with an oxygen-containing gas.

As used herein, the term "anhydrous" includes not only that which is completely free of any water, but also that which is "substantially anhydrous". Minor amounts of water may be present so long as its presence does not result in the formation of a significant amount (e.g., greater than 5 weight-percent) of bismuth hydrate at the elevated temperature of the process of the present invention. The anhydrous condition of the process described herein is an important aspect of the present invention. The inventors have found that by excluding the presence of significant amounts of water, reaction time can be reduced and product properties such as viscosity and color can be improved. The inventors believe that at least to some extent these advantages are due to avoiding formation of significant amounts of a bismuth hydrate intermediate.

The carboxylic acids or anhydrides from which the bismuth carboxylates can be prepared include aliphatic, cycoaliphatic and aromatic mono- and polybasic carboxylic acids. The carboxylic acids or anhydrides can be either natural or synthetic, or mixtures thereof. The acids generally contain at least 2 carbon atoms, preferably at least about 6 carbon atoms, more preferably at least about 8 carbon atoms, and most preferably at least about 10 carbon atoms. The carboxylic anhydrides generally contain at least 4 carbon atoms, preferably at least about 6 carbon atoms, more preferably at least about 8 carbon atoms, and even more preferably at least about 12 carbon atoms. The upper carbon atom limit on the carboxylic acids and anhydrides is preferably up to about 16 carbon atoms, and more preferably up to about 12 carbon atoms when a high bismuth content bismuth carboxylate product which is liquid at about room temperature is desired.

When more than one carboxylic acid or anhydride is employed, it is sometimes advantageous to combine at least one carboxylic acid or anhydride having at least about 6 carbon atoms with at least one carboxylic acid containing as few as from about 2 to about 4 carbon atoms or a carboxylic anhydride having about 4 carbon atoms. Such combinations of at least one lower molecular weight carboxylic acid or anhydride with at least one higher molecular weight carboxylic acid or anhydride have now been found to have the surprising and unexpected advantage of being able to achieve substantial decreases in reaction product viscosity relative to the high viscosity products obtained from the higher molecular weight carboxylic acids or anhydrides used alone while nevertheless maintaining high bismuth salt content. The inventors have found that the lowered viscosity of the reaction product not only enhances the workability of the product, but also influences the rate of reaction, since a lower viscosity during the reaction makes it easier to bring reactants into contact with each other.

Examples of useful carboxylic acids include acetic acid, propionic acid, butyric acid, isopentanoic acid, hexoic acid, 2-ethyl butyric acid, nonanoic acid, decanoic acid, 2-ethylhexoic acid, isooctanoic acid, isononanoic acid, neodecanoic acid, lauric acid, palmitic acid, stearic acid, oleic acid, linoleic acid, naphthenic acid, and commercially available mixtures of two or more carboxylic acids such as naphthenic acid, tall oil acids, rosin acids, malonic acids, succinic acids and anhydrides, especially neodecanoic acid and aliphatic-substituted succinic acids and anhydrides, etc.

It is preferred that the organic acid be aliphatic (straight chain or branched) and it is also preferred that the bonds between the carbon atoms be saturated, rather than unsaturated. The organic acid may be substituted or unsubstituted.

The bismuth metal is preferably present in a form which has a large (surface area):(quantity of bismuth) ratio. One form in which bismuth metal is readily available is that of crystalline needles. Crystalline needles, however tend to be somewhat heavy and difficult to disperse throughout the reaction mixture. A fine bismuth powder is, therefore, preferred, such as a bismuth powder having a Tyler mesh size of up to about $-325$. There is, however, no upper limit on the particle size of the bismuth metal, except for practical considerations having to do with the time required for the reaction to achieve maximum bismuth carboxylate concentration.

A reducing agent is present because the inventors have found that the presence of a reducing agent causes a substantial increase in the rate of the reaction process. Although the inventors do not wish to be bound by a particular theory with regard to how the reducing agent increases the reaction rate, the inventors surmise that the reducing agent reduces bismuth oxide on the surface of bismuth metal, making the bismuth metal more readily available as a metal reactant.

Any reducing agent which is capable of reducing bismuth metal from its higher positive oxidation state to a lower oxidation state may be utilized in the process of the present invention. Examples of such reducing agents include organic reducing agents such as ascorbic acid and oxalic acid and inorganic reducing agents such as sodium bisulfite and various hydrazine sources.

The hydrazine source used in the present invention is a compound or mixture of compounds which is capable of producing hydrazine under the conditions of the reaction in sufficient quantity to reduce the bismuth metal oxide from a higher to a lower positive oxidation state. Many such hydrazine sources are known to those of skill in the art. See, for example, the book entitled "Hydrazine" by Charles C. Clark, published by the Mathieson Chemical Corporation of Baltimore, Md. (1953), particularly pages 31 through 71 and 120 through 124; and the book entitled "The Chemistry of Hydrazine" by L. F. Audrieth and B. A. Ogg, published by John Wiley and Son, New York (1951), especially pages 209 through 223, each of which is incorporated herein by reference. The hydrazine sources are the preferred reducing agents.

Among the more common, and therfore preferred hydrazine sources are hydrazine itself and hydrazine hydrate, as well as hydrazinium salts of, for example, sulfuric and hydrochloric acid, semicarbazides and thiosemicarbazides and their analogous salts; hydrazine dicarboxylates of lower alkanols (e.g., ROOCNHNHOOR wherein R is an aliphatic hydrocarbyl group) and their dimers as well as the amino guanidines and their —NHNH—sulfuric and hydrochloric acid salts and benzene sulfonyl hydrazides and their bisoxy analogs. Mixtures of hydrazine sources can also be used. This list is not intended to be exhaustive or in any way limit the invention and many useful hydrazine sources similar to those listed will occur to those skilled in the art.

For reasons of economy and ease of handling, hydrazine, hydrazine hydrate, and solutions thereof with solvent/diluents are preferred.

The presence of water in the hydrazine hydrate has not caused any problems with respect to the required anhydrous reaction conditions, since only a small amount of the hydrazine is necessary to obtain the desired increase in the process rate of the present invention. An amount of from about 0.5 to about 1.5 weight percent in the reaction mixture is generally sufficient.

Techniques of using such hydrazine sources in chemical reactions are well known to those of skill in the art, as for example is shown by the books cited above and the article entitled "Hydrazine" in Kirk-Othmer Encyclopedia of Chemical Technology, Second Edition, Vol. 11, pages 164–196, Interscience Publishers, New York, N.Y. (1966). These are hereby incorporated by reference for their relevant disclosures in regard to techniques for using hydrazine sources.

The ratio with which the carboxylic acid or anhydride and the bismuth metal are mixed vary over a wide range depending upon the desired bismuth metal content in the product of the reaction process of the present invention. Since a high metal content is generally desired for the types of applications mentioned under the above BACKGROUND OF THE INVENTION, it is generally desirable, although not required, to conduct the process of the present invention with bismuth metal in excess of the amount required to stoichiometrically react with the carboxylic acid or anhydride. Since the bismuth metal is a solid and the desired bismuth carboxylate is generally a liquid either at room temperature or at an elevated temperature, it is a simple matter to separate the desired bismuth carboxylate from the bismuth metal remaining when the process has been completed.

The metal ratio of the bismuth cation to the carboxylic acid or anhydride generally may be as low as about 0.9:1 or as high as about 1.1:1. A metal ratio is defined herein as the ratio of equivalents of bismuth cation to the equivalents of carboxylic acid or anhydride. When, for example, a neutral bismuth carboxylate is prepared, the metal ratio is 1:1 (i.e., one equivalent of bismuth cation per one equivalent of carboxylic acid or anhydride).

The temperature at which the components are reacted to form the bismuth carboxylate product is generally at least about 80° C., but below the decomposition temperature of the components of the reaction mixture and the desired bismuth carboxylate. The decomposition temperature may vary with the particular reactants, concentrations, etc., of each particular synthesis. Generally, it is preferred that the temperature be kept below about 130° C., and more preferably the temperature is kept below about 115° C., since temperatures about 115° C. or greater sometimes cause a color change in the reaction product. Below about 80° C., insufficient product is formed or the reaction rate is so slow as to be impractical, so the range of temperatures for the process is generally from about 80° C. to about 130° C. A preferred temperature is in the range of from about 100° C. to about 110° C. when, for example, operating at atmospheric pressure, since that temperature range is generally well below that which would either decompose the components of the reaction mixture or volatilize a significant portion of the carboxylic acid or anhydride reactant, and is yet a high enough temperature to insure that water generated during the reaction is volatilized and removed by the bubbling of the oxygen-containing gas through the reaction mixture.

The oxygen-containing gas may be any gas which contains oxygen in the form of di-oxygen (i.e., $O_2$). The concentration of oxygen in the oxygen-containing gas is not a critical feature of the invention, but it is desirable from a practical standpoint for a sufficient quantity of oxygen to be present in the oxygen-containing gas to avoid the necessity for bubbling large quantities of the oxygen-containing gas over a long period of time in order to obtain the desired concentration of bismuth carboxylate product. From this practical standpoint, it is desirable to deliver the oxygen-containing gas to the reaction mixture at a rate which delivers at least about 1 gram of oxygen, preferably at least about 2 grams of oxygen, per gram-equivalent of the carboxylic acid or anhydride of (A) per hour.

The inventors have discovered that practical results can be obtained by bubbling air through the reaction mixture with the reaction conducted at atmospheric pressure. The concentration of oxygen in the reaction mixture can, of course, be increased in order to increase the rate of reaction. In one preferred embodiment, the process for making a bismuth carboxylate is conducted under a pressure greater than atmospheric pressure. The reaction can, for example, be conducted in an autoclave, increasing the concentration of oxygen in the reaction by a factor corresponding to the pressure in atmospheres within the autoclave. The increased concentration of oxygen being bubbled through the reaction mixture generally increases the reaction rate.

In another embodiment, the concentration of oxygen in the reaction mixture may be increased by using an oxygen-containing gas having a high concentration of oxygen (i.e., a concentration greater than that found in air). Pure, or substantially pure, oxygen would, for example, provide an oxygen concentration which is approximately 5 times greater than that provided by air at the same pressure, since air contains about 21 mole-percent oxygen.

Step (C) of removing water formed during (B) from the reaction mixture may be performed either during step (B) or as a separate step after (B) is completed.

In one embodiment, step (C) of removing water formed during step (B) from the reaction mixture occurs during step (B) when the oxygen-containing gas bubbling through the reaction mixture according to (B) picks up moisture volatilized in the reaction mixture during (B). This can occur any time the oxygen-containing gas is not saturated with moisture at the reaction temperature of the process. Generally, removal of water from the reaction mixture is aided by bubbling the oxygen-containing gas even when the oxygen-containing gas contains significant amounts of moisture, since in most cases the oxygen-containing gas will undergo an in increase in temperature and decrease in pressure as it passes through the reaction mixture, decreasing the relative humidity of the oxygen-containing gas. This drying effect, of course, can be further augmented by using an anhydrous oxygen-containing gas in step (B). The term "anhydrous" in this context has the same meaning as defined above for "anhydrous reaction mixture" in that it includes "substantially anhydrous" within its scope.

In another embodiment, step (C) may be performed as a separate step after step (B) is completed. If a product is desired which contains minimal amounts of water, the reaction product may be heated to a temperature of at least 100° C., or higher, preferably with bubbling or purging using a gas not saturated with moisture at the elevated temperature, provided that the temperature is below the decomposition temperature of the desired bismuth carboxylate reaction product. Such temperatures may, for example, be as high as 110° C., 120° C., 130° C., 140° C. or higher. The gas may be any gas which is not reactive with the bismuth carboxylate, such as nitrogen gas.

In yet another embodiment, step (C) may be performed by reducing the pressure above the reaction mixture and/or reaction product below atmospheric pressure, preferably while bubbling or purging with a gas as mentioned in the above separate step (C) description. When, for example, the pressure above the mixture is reduced to less than 0.35 atmosphere, the temperature of the reaction mixture and/or reaction product may be as low as 95° C. to provide efficient removal of moisture from the reaction mixture and/or product.

The specific means for conducting step (C) may be determined based upon various practical considerations which are within the skill of the ordinary artisan to determine.

The reaction process of the present invention may be conducted with only the reactants present in the reaction mixture and no additional components. Sometimes it is advantageous, however, to include an inert low viscosity anhydrous liquid diluent having a boiling point of at least about 80° C., preferably at least about 100° C. and more preferably at least about 120° C., in the reaction mixture to facilitate the reaction process and/or reduce the viscosity of the desired bismuth carboxylate reaction product. The term "low viscosity" in this context means that the liquid diluent has a viscosity less than that of the reaction product or the reaction mixture containing the product, which preferably is less than about 500 centipoise, and more preferably is less than about 200 centipoise. The term "anhydrous" again includes "substantially anhydrous" as defined above. Unless otherwise provided in the examples, specification, and claims, the term "centipoise" refers to the viscosity of a liquid material at 25° C. measured with a Brookfield viscometer.

The liquid diluent may, for example, be an organic solvent such as an aliphatic or aromatic hydrocarbon. Mineral spirits, for example, have been found to be particularly useful in view of their low viscosity, inertness and low cost.

In another embodiment of the present invention, the inventors have found that the rate of the overall process of the present invention can be increased by adding a carboxylic acid or anhydride, an inert low viscosity anhydrous liquid diluent, or a mixture thereof to the reaction mixture after the reaction process has been initiated. Small amounts, as low as 10 weight percent or less, preferably 5 weight percent or less, carboxylic acid or anhydride, liquid diluent, or mixture thereof, has been found to result in a significant improvement in the rate of reaction when the reaction is continued after this step. This step can be conducted at any time during the reaction process. Preferably, this diluting step is conducted when the reaction has been underway for at least 5 hours, and preferably for at least 10 hours.

As mentioned above, a surprising and unexpected method of increasing the rate of the present invention discovered by the inventors is that a substantial decrease in reaction product viscosity and a substantial increase in the rate of the process can be obtained by adding small amounts of a low molecular weight carboxylic acid or anhydride to a reaction mixture of (A) containing at least one carboxylic acid or anhydride having from about 6 to about 20 carbon atoms. It has been found, for example, that adding 20 equivalents or less of a carboxylic acid having from 2 to about 4 carbon atoms to a reaction mixture containing at least 80 equivalents of at least one carboxylic acid or anhydride having from about 6 to about 20 carbon atoms, per 100 equivalents of carboxylic acid or anhydride in the reaction mixture, is often capable of reducing the viscosity of the reaction mixture by one-third or more. About 30 equivalents of carboxylic acid having from 2 to about 4 carbon atoms or carboxylic anhydride having about 4 carbon atoms per 100 equivalents of carboxylic acid or anhydride in the reaction mixture is a practical maximum in reaction mixtures containing at least about 70 equivalents of at least one carboxylic acid or anhydride having from about 6 to about 20 carbon atoms, generally because a greater amount of the low molecular weight carboxylic acid generally has a tendency to form precipitates with the bismuth.

Preferably, the reaction mixture contains (1) at least about 80 equivalents, more preferably 90 equivalents, of carboxylic acid or anhydride having from about 6 to about 20 carbon atoms, more preferably from about 8 to about 16 carbon atoms, and (2) up to about 20 equivalents, more preferably up to about 10 equivalents, of carboxylic acid having from 2 to about 4 carbon atoms or carboxylic anhydride having about 4 carbon atoms per 100 equivalents of carboxylic acid or anhydride in the reaction mixture of (A). Generally, the greater the number of carbon atoms of the higher molecular weight carboxylic acid or anhydride and the greater its concentration in the mixture of carboxylic acids and/or anhydrides, the more the mixture can tolerate the presence of the lower molecular weight carboxylic acid or anhydride without forming a precipitate. When more than about 50 equivalents per 100 equivalents of carboxylic acid or anhydride of (A) have from about 6 to about 10 carbon atoms, the ratio of equivalents between the higher and the lower molecular weight carboxylic acids or anhydrides is preferably at least about 80:20.

The resulting bismuth carboxylate preferably has a metal ratio from about 0.9:1 to about 1.1:1 and preferably is a liquid having a viscosity of not more than about 1000 centipoise, preferably not more than about 800 centipoise, and more preferably not more than about 500 centipoise. One preferred aspect of the present invention is a liquid composition having a viscosity of not more than about 1000 centipoise comprising at least one bismuth carboxylate derived from at least one carboxylic acid or anhydride having from about 6 to about 16 carbon atoms, wherein the at least one bismuth carboxylate is present in an amount of at least about 70 weight-percent, preferably at least about 80 weight-percent and more preferably at least about 90 weight-percent, and most preferably at least about 95 weight-percent in terms of the neutral bismuth carboxylate. In a more preferred aspect of the present invention, the liquid composition contains at least 80 weight-percent bismuth carboxylate derived from at least one carboxylic acid having from about 8 to about 12 carbon atoms.

Bismuth carboxylates find utility as a polyurethane catalyst and as a catalyst for gas oil cracking, among other uses. One skilled in the additive art may determine the effect of an economical amount for such uses.

The invention will be further clarified by consideration of the following examples which are intended to be purely exemplary of the use of he invention.

Unless otherwise provided in the examples and elsewhere in the specification and claims, all percentage amounts are expressed as percent by weight and the conditions of pressure and temperature are atmospheric (about one atmosphere) and room temperature (about 25° C.).

EXAMPLE I

A 4.0 liter reaction flask equipped with heating mantle, sparging tube, temperature controller, impeller and a Dean and Stark type condensing tube (whereby vaporized water ma be condensed and drained away from the reaction system) is charged with 2500 grams of neodecanoic acid, 700 grams bismuth powder having a mesh size not greater than $-325$, and 48 grams hydrazine hydrate (30%). The batch is mixed and sparged with air at 104° C. for 14 hours, and then sparged with nitrogen while dehydrating to 128° C. The product is filtered using a heated Buchner funnel. The filtered product has a viscosity of approximately 2,000 centistokes and a specific gravity at 25° C. of 1.138, so that the viscosity in centipoise is 2,276. This product may be diluted with additional neodecanoic acid, low viscosity liquid diluent, etc., to achieve a desired viscosity less than about 1,000 centipoise.

EXAMPLE II

A 2.0 liter reactor flask equipped with heating mantle, sparging tube, temperature controller, impeller and condensate receiver with condenser (whereby vaporized water may be condensed and drained away from the reaction system) is charged with 454 grams of 2- ethylhexoic acid, 80 grams of propionic acid, 300 grams of mineral spirits, and 260 grams of bismuth powder followed by 1 gram of hydrazine hydrate. The reactor is heated to 82° C. while being sparged with air at the rate of 85 liters per hour. The reactor is maintained at this temperature and sparging is continued for a period of 16 hours. Sparging with air is then discontinued, the temperature of the material in the reactor is slowly raised to 127° C. under nitrogen bleed, and the residual water and solvent are removed by vaccuum stripping (i e., continued heating under reduced pressure to as low as 0.35 atmosphere (260 Torr) while expelling volatile components from the reaction mixture) to yield a product containing 31.9 percent bismuth octoate in terms of bismuth metal and having a viscosity of 100 centipoise.

Other embodiments of the invention will be apparent to one skilled in the art from a consideration of this specification or practice of the invention disclosed herein. It is intended that the specification and examples be considered as exemplary only, with the true scope and spirit of the invention being indicated by the following claims.

We claim:

1. A process for making a bismuth carboxylate reaction product comprising:
   (A) heating an anhydrous reaction mixture comprising a carboxylic acid or anhydride, bismuth metal, and a reducing agent to a temperature of from about 80° C. up to, but not including, the temperature of decomposition of any reactant, the reducing agent or the desired bismuth carboxylate;
   (B) bubbling an oxygen-containing gas through the reaction mixture during (A); and
   (C) removing water formed during (B) from the reaction mixture and/or reaction product.

2. The process of claim 1 wherein (C) comprises raising the temperature of the mixture to at least 100° C.

3. The process of claim 1 wherein (C) comprises reducing the pressure above the mixture below atmospheric pressure and raising the temperature of the mixture to at least 95° C.

4. The process of claim 3 wherein (C) comprises reducing the pressure above the mixture to less than 0.35 atmosphere.

5. The process of claim 1 wherein (C) comprises conducting (B) using an anhydrous oxygen-containing gas.

6. The process of claim 1 further comprising:
   (D) separating the bismuth carboxylate formed during the reaction from any unreacted components of the reaction mixture.

7. The process of claim 1 wherein the carboxylic acid of (A) has from about 2 to about 20 carbon atoms and the carboxylic anhydride of (A) has from about 4 to about 20 carbon atoms.

8. The process of claim 7 wherein the carboxylic acid or anhydride of (A) has from about 6 to about 20 carbon atoms.

9. The process of claim 7 wherein the carboxylic acid or anhydride of (A) has from about 8 to about 16 carbon atoms.

10. The process of claim 1 wherein the carboxylic acid or anhydride of (A) present in the reaction mixture when (B) is initiated comprises a mixture having (1) at least 70 equivalents carboxylic acid or anhydride having from about 6 to about 20 carbon atoms and (2) up to about 30 equivalents carboxylic acid having from 2 to about 4 carbon atoms or carboxylic anhydride having about 4 carbon atoms, per 100 equivalents of the carboxylic acid or anhydride.

11. The process of claim 1 wherein the carboxylic acid or anhydride of (A) is a monocarboxylic acid or anhydride.

12. The process of claim 1 wherein the carboxylic acid or anhydride of (A) is a polycarboxylic acid or anhydride.

13. The process of claim 1 wherein the bismuth metal of (A) is a finely divided powder having a Tyler mesh size of up to about −325.

14. The process of claim 1 wherein the bismuth metal of (A) is in crystalline needle form.

15. The process of claim 1 wherein the reaction mixture of (A) comprises an amount of bismuth metal in excess of the amount required to stoichiometrically react with the carboxylic acid or anhydride.

16. The process of claim 1 wherein the reaction mixture of (A) further comprises an inert low viscosity anhydrous liquid diluent having a boiling point of at least about 80° C.

17. The process of claim 16 wherein the diluent comprises an aliphatic or aromatic hydrocarbon.

18. The process of claim 16 wherein the diluent comprises mineral spirits.

19. The process of claim 1 further comprising
   (D-1) adding a carboxylic acid or anhydride, an inert low viscosity anhydrous liquid diluent, or a mixture thereof to the reaction mixture after initiation of (B).

20. The process of claim 19 further comprising
   (D-2) continuing (B) after (D-1).

21. The process of claim 20 wherein (D-1) is carried out after (B) has been conducted for at least 5 hours.

22. The process of claim 1 wherein (B) is conducted at a rate which delivers at least about 1 gram of oxygen per gram-equivalent of the carboxylic acid or anhydride of (A) per hour.

23. The process of claim 1 wherein the oxygen-containing gas of (B) is air.

24. The process of claim 1 wherein (A) is conducted at a temperature of from about 80° C. to about 130° C.

25. The process of claim 1 wherein (A) is conducted at a temperature of from about 100° C. to about 110° C.

26. The process of claim 1 wherein the bismuth carboxylate reaction product has a metal ratio in the range from about 0.9 to about 1.1 when the process is terminated.

27. The process of claim 1 wherein at least 80 weight-percent of the carboxylic acid or anhydride of (A) present in the reaction mixture when (B) is initiated is converted to the bismuth carboxylate when the process is terminated.

28. The process of claim 27 wherein at least 80 equivalents of the carboxylic acid or anhydride per 100 equivalents of the carboxylic acid of anhydride of (A) has from about 6 to about 20 carbon atoms .

29. The process of claim 27 wherein the viscosity of the reaction product is no more than about 1000 centipoise when the process is terminated.

30. A process for making a bismuth carboxylate reaction product comprising:
   (A) heating an anhydrous reaction mixture comprising a carboxylic acid or anhydride, bismuth metal, and a hydrazine source to a temperature of from about 80° C. up to, but not including, the temperature of decomposition of any reactant, hydrazine or the desired bismuth carboxylate;

(B) bubbling an oxygen-containing gas through the reaction mixture during (A); and (C) removing water formed during (B) from the reaction mixture and/or reaction product wherein the carboxylic acid or anhydride of (A) present in the reaction mixture when (B) is initiated comprises a mixture having (1) at least 70 equivalents carboxylic acid or anhydride having from about 6 to about 20 carbon atoms and (2) up to about 30 equivalents carboxylic acid having from 2 to about 4 carbon atoms or carboxylic anhydride having about 4 carbon atoms, per 100 equivalents of the carboxylic acid or anhydride, at least 80 weight-percent of the carboxylic acid or anhydride of (A) present in the reaction mixture when (B) is initiated is converted to the bismuth carboxylate when the process is terminated, and the viscosity of the reaction product is not more than 1000 centipoise when the process is terminated.

31. A process for making a bismuth carboxylate reaction product comprising:
(A) heating an anhydrous reaction mixture comprising a carboxylic acid or anhydride, bismuth metal, and a hydrazine source to a temperature of from about 80° C. up to, but not including, the temperature of decomposition of any reactant, hydrazine or the desired bismuth carboxylate;
(B) bubbling an oxygen-containing gas through the reaction mixture during (A); and
(C) removing water formed during (B) from the reaction mixture and/or reaction product wherein the carboxylic acid or anhydride of (A) has from about 8 to about 16 carbon atoms, the reaction mixture of (A) comprises an amount of bismuth metal in excess of the amount required to stoichiometrically react with the carboxylic acid or anhydride, and the process further comprises:

(D-1) adding a carboxylic acid or anhydride, an inert low viscosity anhydrous liquid diluent, or a mixture thereof to the reaction mixture after initiation of (B) and (D-2) continuing (B) after (D-1).

32. A liquid composition having a viscosity of not more than about 1000 centipoise comprising at least one bismuth carboxylate derived from at least one carboxylic acid or anhydride having from about 6 to about 16 carbon atoms wherein the at least one bismuth carboxylate is present in an amount of at least about 70 weight-percent in terms of the neutral bismuth carboxylate.

33. The liquid composition of claim 32 wherein the viscosity of the composition is not more than about 800 centipoise.

34. The liquid composition of claim 32 wherein the at least one bismuth carboxylate is derived from at least one carboxylic acid or anhydride having from about 8 to about 12 carbon atoms present in an amount of at least 90 weight-percent in terms of the neutral bismuth carboxylate.

35. The liquid composition of claim 32 wherein the liquid composition is free of low viscosity liquid diluent.

* * * * *